(12) United States Patent
Hallander et al.

(10) Patent No.: US 9,101,332 B2
(45) Date of Patent: Aug. 11, 2015

(54) MEDICAL IMPLANTABLE LEAD WITH FIXATION DETECTION

(71) Applicant: ST. JUDE MEDICAL AB, Jarfalla (SE)

(72) Inventors: Sara Hallander, Alvsjo (SE); Marcus Helgesson, Danderyd (SE)

(73) Assignee: ST. JUDE MEDICAL AB, Jarfalla (SE)

( * ) Notice: Subject to any disclaimer, the term of this patent is extended or adjusted under 35 U.S.C. 154(b) by 0 days.

(21) Appl. No.: 14/518,870

(22) Filed: Oct. 20, 2014

(65) Prior Publication Data

US 2015/0038821 A1 Feb. 5, 2015

Related U.S. Application Data

(62) Division of application No. 13/509,530, filed as application No. PCT/SE2009/051356 on Nov. 30, 2009, now Pat. No. 8,903,514.

(51) Int. Cl.
*A61N 1/00* (2006.01)
*A61B 5/00* (2006.01)
*A61N 1/05* (2006.01)
*A61B 5/04* (2006.01)

(52) U.S. Cl.
CPC ............. *A61B 5/6882* (2013.01); *A61B 5/6869* (2013.01); *A61N 1/05* (2013.01); *A61N 1/0573* (2013.01)

(58) Field of Classification Search
CPC .... A61B 5/042; A61B 5/6852; A61B 5/6869; A61B 2018/00279; A61B 2018/00357; A61B 2018/1435; A61N 1/0573
USPC ................. 600/372–377, 381, 393, 508–509; 607/115–116, 119, 123, 125–127, 131; 606/41
See application file for complete search history.

(56) References Cited

U.S. PATENT DOCUMENTS

| 5,480,420 | A | 1/1996 | Hoegnelid et al. |
| 5,716,391 | A | 2/1998 | Grandjean |
| 6,931,286 | B2 * | 8/2005 | Sigg et al. ..................... 607/120 |
| 7,991,484 | B1 | 8/2011 | Sengupta et al. |
| 2009/0240315 | A1 * | 9/2009 | Bischoff et al. ............... 607/116 |
| 2011/0130752 | A1 * | 6/2011 | Ollivier .......................... 606/33 |

FOREIGN PATENT DOCUMENTS

WO WO2007073435 * 6/2007

OTHER PUBLICATIONS

Notice of Allowance, mailed Jul. 18, 2014—Parent U.S. Appl. No. 13/509,530.

* cited by examiner

*Primary Examiner* — Joseph Stoklosa
*Assistant Examiner* — Brian M Antiskay

(57) ABSTRACT

A lead comprises a mechanical switch at a proximal end of a rotatable shaft. The mechanical switch has a first position to electrically connect a first electric conductor to a second electric conductor for electrically activating a pin and has a second position to electrically connect the first electric conductor to the rotatable shaft for electrically activating a helix. Proper fixation of the helix to an organ is determined by inserting a stylet into the mechanical switch to render the pin electrically active and the helix electrically inactive. Upon determination of proper fixation of the helix to the organ, the stylet is removed from the mechanical switch to render the helix electrically active and the pin electrically inactive.

9 Claims, 8 Drawing Sheets

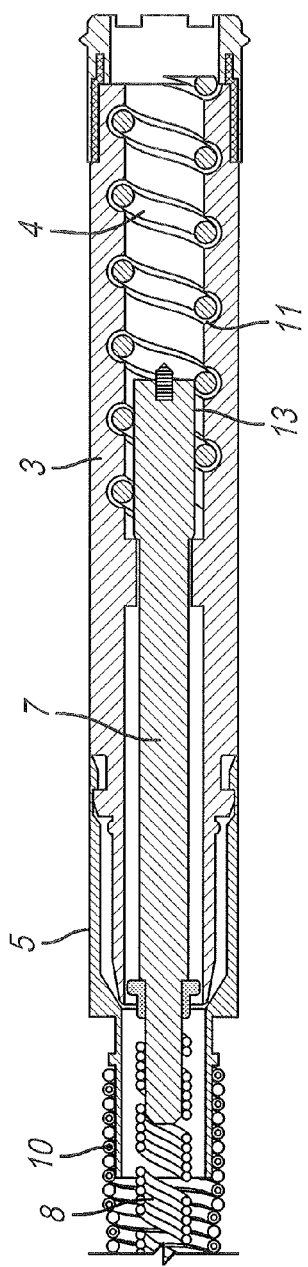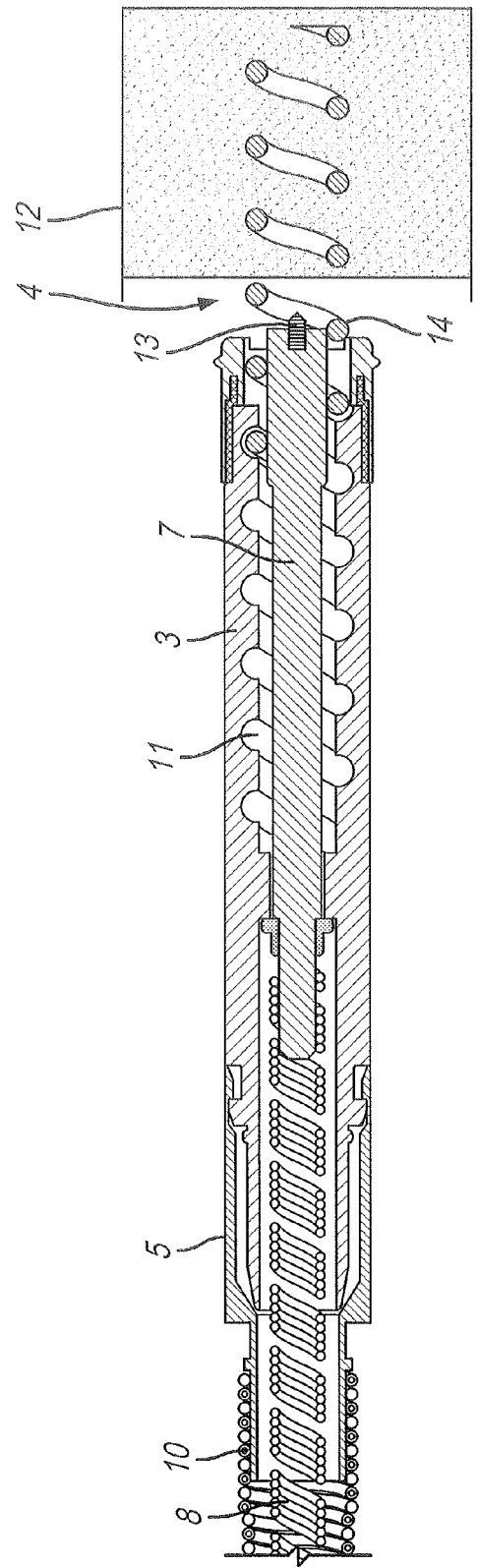
FIG. 3
FIG. 4

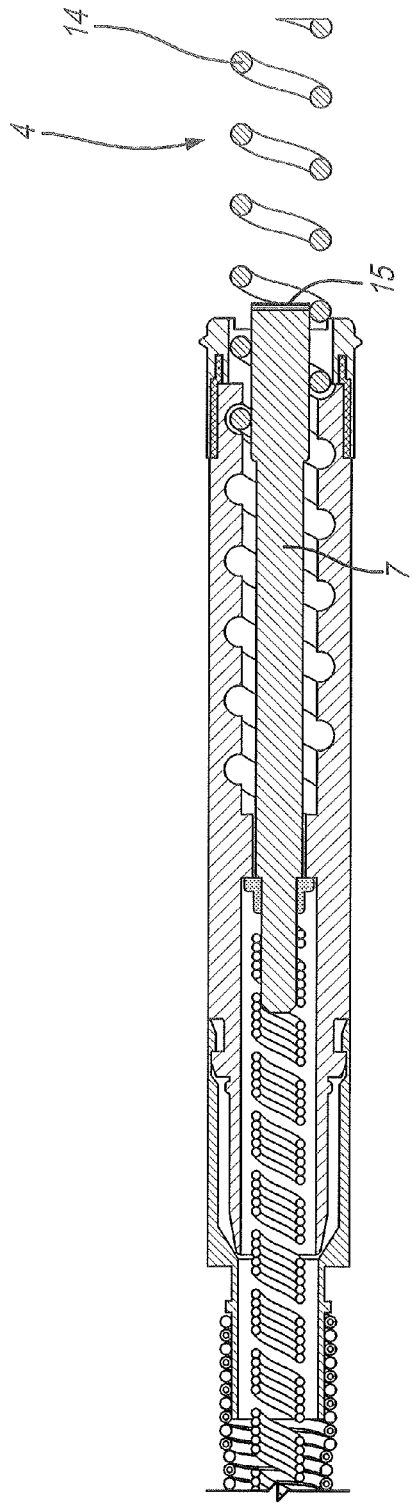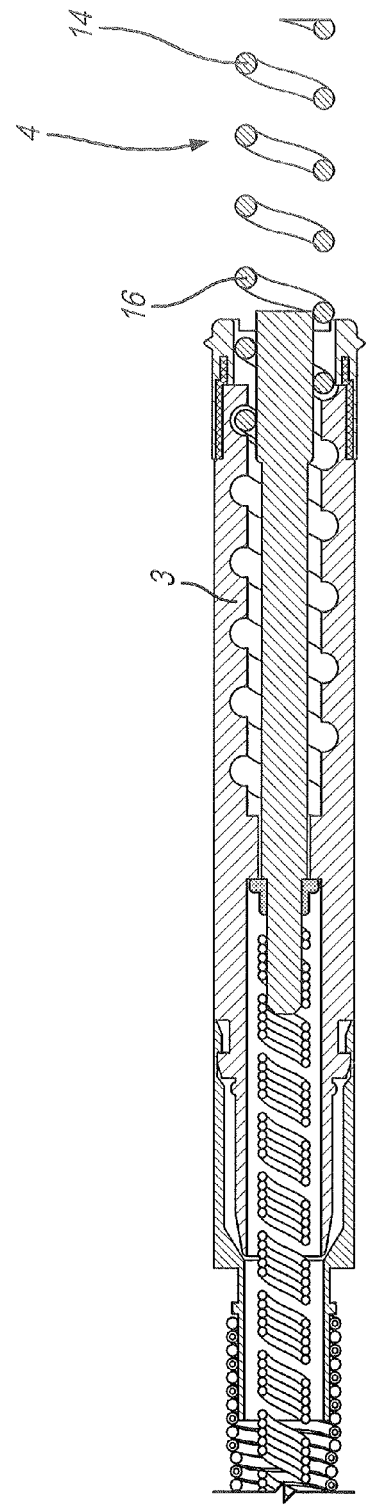

MEDICAL IMPLANTABLE LEAD WITH FIXATION DETECTION

CROSS REFERENCE TO RELATED APPLICATIONS

This application is a division of U.S. patent application Ser. No. 13/509,530, filed May 11, 2012, which is a 371 of International Application No. PCT/SE09/051356, filed Nov. 30, 2009.

FIELD OF THE INVENTION

The present invention relates to a medical implantable lead of the kind being adapted to be implanted into a human or animal body for monitoring and/or controlling of an organ inside the body, comprising in a distal end a tubular header inside which a shaft is rotatable as well as extendable and retractable arranged and carries in a distal end a combined fixation means and electrode member in form of a helix, which is provided with a first contact surface being electrically connectible to a connector at the proximal end of the lead by means of an electric conductor, and which by means of the shaft is rotatable in relation to the lead and extendable out from the distal end to be able to fixate the distal end of the lead to the organ by being screwed into the tissue, wherein the shaft also is provided with a second contact surface being positioned on or adjacent a proximal portion of the helix which is located beyond the distal end of the shaft and being connectible to a connector at the proximal end of the lead by means of an electric conductor.

BACKGROUND OF THE INVENTION

Implantable medical leads having a helix, which is rotatable as well as extendable out from and retractable into a tubular header in the distal end of the lead, and which functions both as a fixation means, for attaching to the tissue of an organ inside a body, and an electrode member for transmitting and/or receiving electrical signals to and from the organ, are well known in prior art. Such medical implantable leads are e.g. used to connect a pacemaker or a cardiac defibrillator device to a heart, but also other applications for monitoring and/or controlling the function of other organs could be conceivable with such a lead.

Normally, such a medical implantable lead is implanted from the outside of the body. For example in case of a pacemaker, the lead can be introduced into a heart through a vein and attached to the inner surface of a heart wall. The physician performing the implantation cannot actually see when the implantation is performed other than by means of x-ray imaging and accordingly it is hard to verify the performance of the attachment.

It can be extremely important for a patient that the fixation of the helix is done properly, both in relation to transmitting of electrical signals between the tissue and the helix as well as in relation to long term secure attachment of the lead to the organ such that the lead is not accidently disengaged from the organ. Poor helix fixation is a well known problem and till now there has been no good way of verifying whether a helix is properly secured to the tissue or not. In prior art it has been known to e.g. perform current of injury measurements, i.e. to measure the potential difference between injured tissue, e.g. tissue which is penetrated by a helix, and uninjured tissue, or to perform mechanical pull tests of the attached lead. Both of these methods are associated with drawbacks since they can appear to indicate a proper fixation even when only a small part of the helix actually is secured to the tissue. Also, by manufacturing the header and the helix of a radiopaque material it is, by means of x-ray imaging, possible to see when a helix is sufficient screwed out from the header by counting the number of wire loops that is visible beyond the distal end of the header. However, by this method it is not possible to see whether these wire loops are embedded into tissue or not, since the tissue itself is not visible on the images. Another way of ensuring that the helix is sufficient screwed out from the header is to count the number of turns the physician is rotating a helix rotating control member when performing the screwing out of the helix from the proximal end. Due to occurring elastic properties in a rotatable torque transferring member, usually a rotatable wire coil, extending from the helix rotating control member to the shaft, and friction between the torque transferring member and the rest of the surrounding lead, it is however necessary to rotate the helix rotating control member more than the theoretically required number of turns to be sure that the helix will be sufficient screwed out. This result in a risk that the helix my become completely screwed out while the physician continuous to rotate the helix rotating control member such that the distal end of the whole lead is twisted and may perforate e.g. a heart wall.

SUMMARY OF THE INVENTION

It is an object of the invention to provide a medical implantable lead, according to the introductory part, by means of which it is possible to detect whether the helix is sufficient screwed into and embedded in tissue or not. At least this object is achieved by a medical implantable lead according to claim 1.

Accordingly, the basis of the invention is the insight that this object may be achieved by providing the helix or the shaft, in addition to a first contact surface on the helix, with also a second contact surface being located sufficient far in the proximal direction of the lead from the distal tip of the helix and more precisely in or adjacent a proximal portion of the helix which is located beyond a distal end of the shaft. Moreover, the first contact surface on the helix is electrically inactive at least during an initial stage during implantation of the lead in the body.

Within this overall idea, the invention may be varied and modified in many different ways within the scope of the invention. An important feature of the invention is that the second contact surface has to be provided, permanently or temporarily, on the helix or on the shaft or on some other member which is moved together with the shaft and the helix during rotation and extending of the helix when implanting the lead into the body. Moreover, the second contact surface has to be positioned on or at a proximal portion of the helix, more precisely on or at a portion from the distal end of the shaft to half the length of the helix, preferably from the distal end of the shaft to 25% of the length of the helix and most preferred from the distal end of the shaft to 10% of the length of the helix. Accordingly, the second contact surface cannot be arranged on for example the distal end surface of the header since that surface may come into contact with the tissue even though the helix is not completely screwed out from the header. Also, it is to be understood that in case of a unipolar lead, these first and second contact surfaces will be sufficient. However, in addition to the first and second contact surfaces, the lead can also be provided with one more electrode surface in case of a bipolar lead, two or more electrode surfaces in case of a tripolar lead, etc.

In one embodiment of the invention, a first contact surface at a distal portion of the helix is initially inactivated by being coated with an electrically insulating layer of a biologically dissolvable substance, and hence not electrically conducting, while a second contact surface at a proximal portion of the helix is active, and hence electrically conducting, by being free from any electrical insulation. When implanting the lead, it is possible to detect, by electric measurements, if the helix is so far screwed into the tissue such that the second contact surface at the proximal portion of the helix is in contact with the tissue or not. After having been embedded a while in the tissue, the time being determined by the specific biological dissolvable material being used and the thickness of the layer, the insulation layer on the distal portion of the helix will begin to dissolve and vanish such that also the distal portion of the helix will gradually begin to be electrically conducting. In this embodiment it is not necessary to separate the first and second contact surfaces on the helix by well defined limits. Instead they may represent one and the same continuous electrode surface of which a distal portion, i.e. which represents the first contact surface, is coated with an electrically insulating layer of a biologically dissolvable material, while a proximal portion, which represents the second contact surface, is free from any electrically insulating layer.

In an alternative embodiment at least the entire part of the helix which protrudes beyond the distal end of the header in the screwed out condition of the helix, is coated with an electrically insulating layer of a biologically dissolvable material. The second contact surface, on the other hand, is arranged on or carried elsewhere on the rotatable and extendible shaft which also carries the helix. Such a contact surface can be formed as a separate contact member protruding from the shaft or just constitute the whole or a part of the end surface of the shaft. In the former case the contact member usually is formed for and adapted to penetrate into the tissue when implanting the lead, and for this reason it is important that it is coaxially arranged in relation to the helix because otherwise the contact member will tear up a wound in the tissue when rotating the shaft and the helix. In the latter case the contact surface will have the function of a contact surface adapted to transmit signals by abutment against the surface of the tissue and for this reason it is not critical that the contact surface is coaxially arranged in relation to the helix even though this is preferred. Neither of these embodiments requires that the first and second contact surfaces are part of different electric circuits.

In yet another embodiment, the first and second contact surfaces are electrically insulated in relation to each other and are part of different electric circuits. One way of accomplish this is to connect the first and second contact surfaces to an electric connector in the proximal end via a common electric conductor and arrange an electric switch close to the distal end of the lead, preferably at the proximal end of the header. By means of the switch it is possible to choose which one of the first or second contact surfaces that should be connected to the connector in the proximal end of the lead. Accordingly, it is necessary to connect the first and second contact surfaces, respectively, to the switch by means of separate electric conductors which are electrically insulated in relation to each other and also the first and second contact surfaces have to be electrically insulated in relation to each other. However, the first contact surface does not have to be coated by an electrically insulating layer of a biologically dissolvable material, as in the previous embodiments. The switch can be of an electrically operable type, for example as is disclosed in U.S. Pat. No. 5,423,873 or U.S. 2008/0294218 A1, or be of a mechanically operable type which e.g. is shifted by means of a stylet or the like which is introduced through a tubular bore arranged axially in the center of the lead. The stylet may optionally shift the switch by e.g. a rotational or a pushing movement. By means of a medical implantable lead arranged in this way, it is possible for a physician to repeatedly switch between a fixation confirmation state, when the second contact surface is connected to the connector in the proximal end, and an operating state, when the first contact surface is connected to the connector in the proximal end.

Also in a further embodiment, the first and second contact surfaces are electrically insulated in relation to each other and are part of different electric circuits. However, in this embodiment the first and second contact surfaces are also connected to the proximal end of the lead by means of different conductors. The conductor to the second contact surface can be a permanent conductor, e.g. in form of one additional electric wire in a wire coil extending from the header to the proximal end and connected to a separate connector surface in the proximal end. However, the conductor to the second contact surface could also be a temporary conductor, e.g. an electrically conducting stylet which is temporarily introduced into the axially center bore in the lead and which is utilized to perform measurements during implantation stage, for confirmation that the helix is screwed sufficient deep into the tissue, and subsequently is removed.

In a still further embodiment, the lead is provided with a continuous through bore from the proximal to the distal end, i.e. also through the shaft, such that a temporary conductor in form of a stylet is insertable through the bore for contact with or penetration into the tissue. Accordingly, in this embodiment the stylet will function not only as a conductor, but also its distal end will function as the second contact surface and its proximal end will function as a connector to be connected to a measuring device. In order to prevent too deep penetration into the tissue, the stylet should be provided with some kind of stop member, which can engage with a mating stop member of the lead. In the hereinafter illustrated and described embodiment, the stop member on the stylet is in form of a shoulder portion near its distal end which engages a corresponding shoulder portion inside the bore. However, the stop members could be formed in many different ways, e.g. as a pin on the stylet, and be positioned also at other locations, e.g. in its proximal end. To prevent electric contact with conductors within the bore or with the shaft, the stylet could be provided with an electrically insulating layer except in its distal end, which is adapted to function as the second contact surface, and in its proximal end, which is adapted to function as a connector. The stylet could preferably be formed of or comprise a radiopaque material to visually be able to determine whether it is correct positioned or not.

It is to be understood that the electric measuring of whether the second contact surface is electric contact with the tissue or not, can be carried out in different ways and by means of different equipment. In case of a medical implantable lead connected to a heart, it is possible to use a so called Pacing System Analyzer (PSA) and, via the second contact surface, detect a sufficient R-wave amplitude which would indicate a proper contact with the tissue. Using the PSA it is also possible to send out pace pulses that would enter the heart muscle via the second contact surface and a proper voltage capture level will indicate a secure helix engagement to the heart tissue. When using a penetrating member, such as a pin or a stylet, as a second contact surface, it would also be possible to detect a current of injury signal from the injured cells in the tissue, which would indicate a proper attached helix.

The invention will hereinafter be explained with reference to a medical implantable lead adapted to be attached in its distal end to the tissue within a heart and connected to a pacemaker or a cardiac defibrillator device in its proximal end. However, as mentioned hereinbefore, also other types of medical implantable leads for other purposes and connected to other organs within a human or animal body, could be conceivable. It is also to be understood that the embodiments are only examples and that the invention could be varied and modified in also many other ways within the scope of the claims.

BRIEF DESCRIPTION OF THE DRAWINGS

Different embodiments of the invention will hereinafter be described in detail with reference to the accompanying drawings, in which:

FIG. 3 is a longitudinal section through a distal end of a medical implantable lead according to a first embodiment, with the helix in a retracted state;

FIG. 4 is a longitudinal section according to FIG. 3 with the helix in a completely extended state, however incompletely screwed into the tissue;

FIG. 7 is a longitudinal section through a distal end of a lead according to a second embodiment;

FIG. 8 is a longitudinal section through a distal end of a lead according to a third embodiment;

DETAILED DESCRIPTION OF EMBODIMENTS OF THE INVENTION

Figure 1:
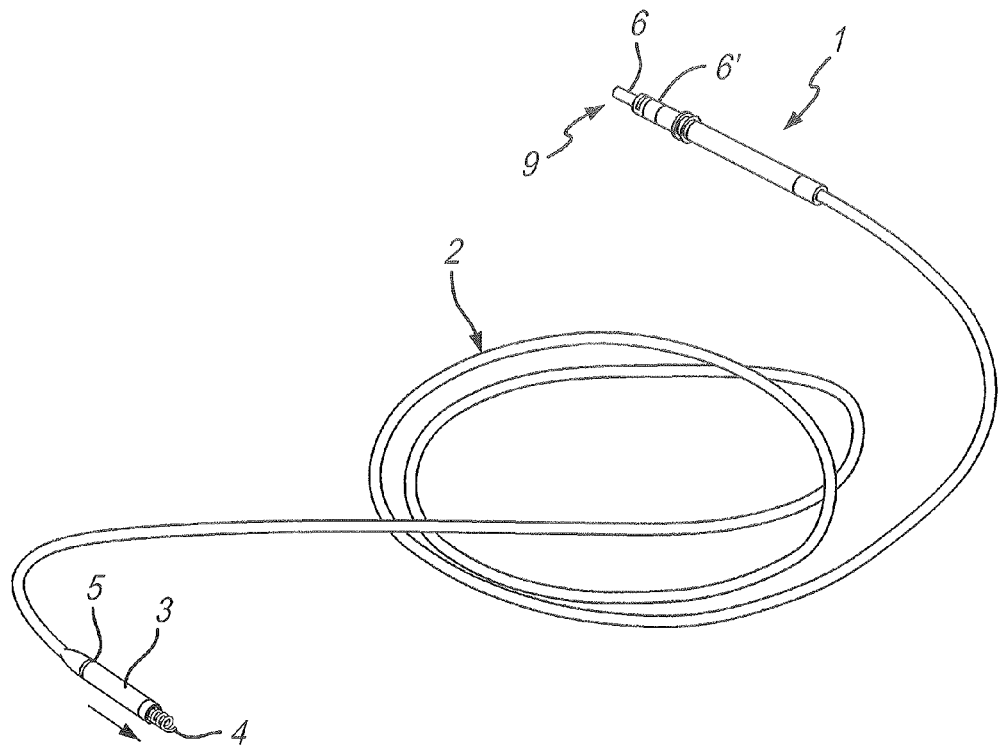
FIG. 1 is a perspective view of a medical implantable lead with the helix in an extended state in the distal end.
Figure 2:
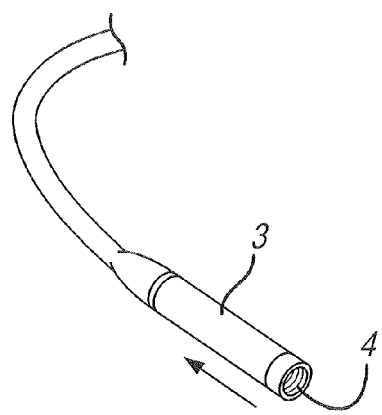
FIG. 2 is a perspective view of the distal end of the lead in FIG. 1 with the helix in a retracted state.

FIG. 1 illustrates in a perspective view, the exterior appearance of an exemplary medical implantable lead according to the invention. The lead comprises in a proximal end a connecting structure 1 for connection to a not shown monitoring and/or controlling device such as a pacemaker, a cardiac defibrillator device or the like, an intermediate flexible lead part 2, and a so called header 3 in a distal end. The header is provided with a helix 4, which can be screwed out in the axial direction of the lead from a cavity in the distal end of the header. The helix has the function of attaching the distal end of the lead to the heart, by being screwed into the tissue, and also functions as an electrode for receiving and/or transmitting electrical signals from and to the tissue, respectively. The header is also provided with a second electrode, a so called indifferent electrode 5, which is positioned a small distance from the distal end and has the purpose of forming a complete current path together with the helix. The helix 4 and the indifferent electrode 5 are each electrically connected to a first and second connector 6, 6', respectively, in form of electric contact surfaces at the connecting structure 1 by means of electric conductors within the lead. In FIG. 1 the helix is illustrated in an extended state, whereas the helix is retracted into the cavity of the header in FIG. 2. The retracted state is assumed during insertion of the lead to the intended position inside a human or animal body and once the distal end has reached the intended position of implantation, the helix is screwed out from the header and into the tissue for attaching the lead to an organ.

Figure 5:
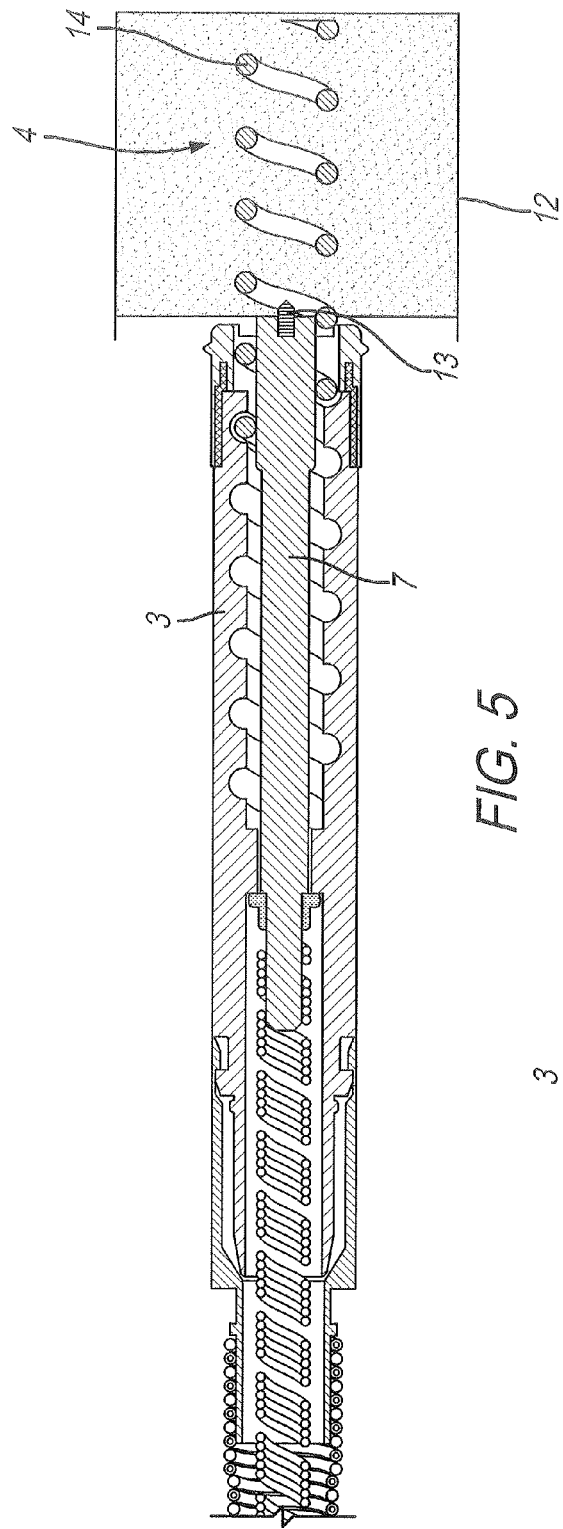
FIG. 5 is a longitudinal section according to FIGS. 3 and 4 with the helix in a completely extended state as well as completely screwed into the tissue.
Figure 6:
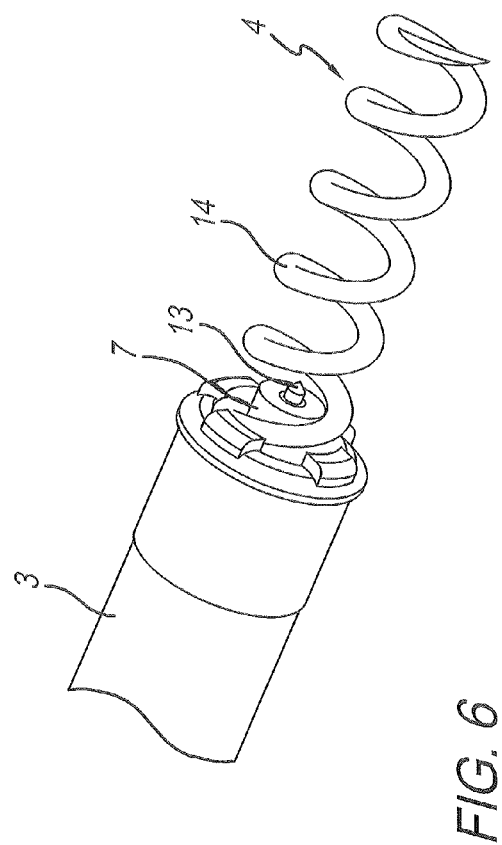
FIG. 6 is a perspective view of the distal end of the lead according to FIGS. 3-5 with the helix in a completely extended state.

Next, reference is made to FIGS. 3-6, in which is illustrated a first embodiment of the invention in longitudinal sections, in FIGS. 3-5, through the distal end of the lead and in a perspective view in FIG. 6. As is commonly known in the art, the helix 4 is attached to an electrically conducting shaft 7, which is rotatable and displaceable within the header 3. In a proximal end, the shaft 7 is connected to a torque transferring member, which in the illustrated embodiment also function as conductor since it is formed as a wire coil 8 composed of at least one electrically conducting wire and can be rotated by rotating a control pin 9 (FIG. 1) in the proximal end of the lead. The wire coil 8 connects the helix to the first connector 6 on the control pin 9. In addition to the inner wire coil 8, the lead also comprises a second, outer wire coil 10, which connects the indifferent electrode 5 to the second connector 6'. The helix is journal led in a helicoidal groove 11 on the inside of the header. Accordingly, when rotating the shaft 7 by means of the inner wire coil 8, and hence also the helix 4, the shaft and the helix will be extended from the retracted position illustrated in FIG. 3, which position is maintained during insertion of the lead into a body, e.g. through a vein or the like, to the fully extended position illustrated in FIGS. 4 and 5. Since the helix is electrically conducting and will function as an electrode, it is important that an as large part as possible of the helix is screwed into and embedded within the tissue 12 of a heart, as is illustrated in FIG. 5. However, although the helix is fully screwed out from the header, a situation as illustrated in FIG. 4 could occur, i.e. the helix 4 is fully screwed out but only a part of the helix is screwed into the heart tissue 12 and the distal end of the header 3 is positioned with a distance from the tissue surface. This situation has the disadvantage that the electric contact between the helix and the tissue is reduced and also that the mechanical attachment of the lead to the tissue will be poor such that there is a risk that the lead could be accidentally detached from the tissue during use. Moreover, this situation is hard and many times even impossible to detect for a physician performing the implantation. It is often possible to ensure that the helix is fully screwed out from the header but, since the tissue is invisible on traditional x-ray imaging and the mechanical attachment could withstand a traditional pulling test, it is in prior art not possible to detect whether the helix is satisfactory screwed into the tissue or not.

For this reason, the medical implantable lead is provided, in addition to a first electric contact surface on the helix, with an additional electric contact surface on a distance from the tip of the helix, which in the embodiment according to FIGS. 3-6 is formed as a pin 13 positioned centrally on the distal surface of the shaft. The pin is in electric contact with the shaft 7, i.e. has the same electric potential as the helix. By means of the pin it is thus possible to detect whether the helix is screwed into the tissue to such an extent that also the pin is in electric contact with the tissue or not. However, in order to allow such a detection, it is necessary that the helix is not electric conducting at that moment. For this reason the helix in this embodiment is coated with a biologically dissolvable layer 14, which during and a short period after implantation will insulate the helix electrically from the tissue. During this helix insulating period it is possible to detect by means of some kind of electric measuring device, when the pin 7 will come into electric contact with the tissue 12 and then there is no doubt that the helix is screwed sufficient far into the tissue. When the medical implantable lead has been implanted in the body for a suitable time period, the electrical insulating layer 14 over the helix 4 will be dissolved and the helix can start functioning as an electrode in the tissue. The length of the time period during which the electric insulating layer is effective may be altered by selecting different materials by which the electric insulating layer is composed of and the thickness of the layer.

In FIG. 7 is disclosed a second embodiment of the invention which is similar to the embodiment according to FIGS. 3-6. However, in this embodiment the shaft 7 is not provided with a pin. Instead the distal end of the shaft is formed with a planar contact surface 15 which, when the helix is correct mounted, will abut against and make electric contact with the surface of the tissue, which is detectable by means of an electric measuring device. As in the embodiment according to FIGS. 3-6, the helix is coated by an electrically insulating layer 14 of a biologically dissolvable material.

FIG. 8 illustrates a third embodiment by which the shaft is not provided with an auxiliary contact surface, like the pin and the planar contact surface of the first and second embodiments according to FIGS. 3-6 and 7, respectively. Like these embodiments, the helix 4 is coated with an electrically insulating layer 14 of a biologically dissolvable material. However, in this embodiment only a distal portion of the helix is coated with an electrically insulating layer, whereas the most proximal portion 16 of the helix a short distance beyond the distal end of the header has no insulating layer but is electrically conducting already at the point of time for implantation. Accordingly, if the lead is correctly implanted the physician performing the implantation may get an indication of this by measurement by means of an electric measuring device since the proximal portion 16 of the helix having no electrically insulating layer will be in electric contact with the tissue. On the contrary, if the lead is incorrectly implanted such that only the distal portion of the helix having an electrically insulating layer 14 is screwed into the tissue, the physician can detect this since there will be no electrical connection between the helix and the tissue upon measurement.

Figure 9:
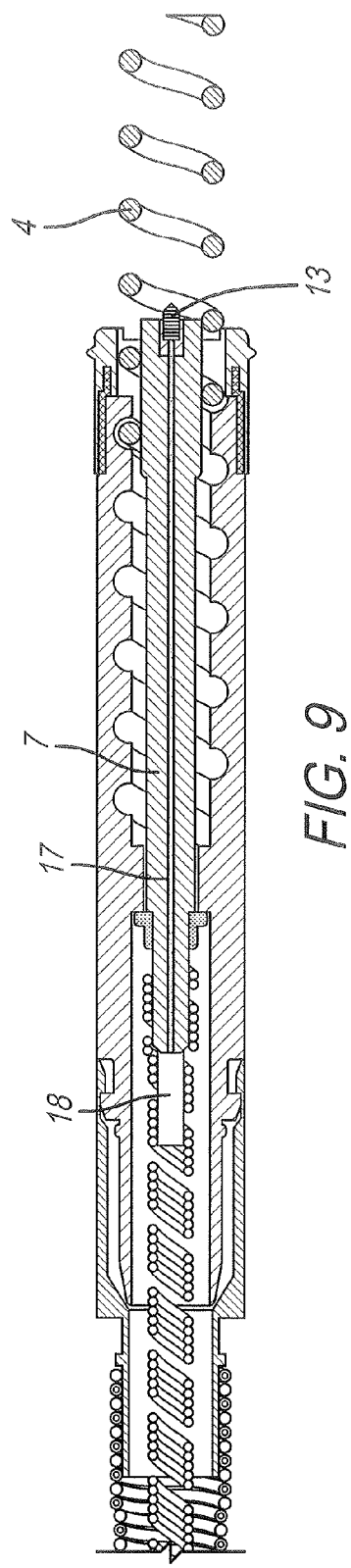
FIG. 9 is a longitudinal section through a distal end of a lead according to a fourth embodiment.

A fourth embodiment of the invention is illustrated in FIG. 9. Here, the helix has no electrically insulating layer of a biologically dissolvable material, as in the previous embodiments. Instead, the shaft 7 is provided with a pin 13 in its distal end which is electrically insulated from the shaft. A separate insulated conductor 17 is arranged in a central passage in the longitudinal direction of the shaft between the pin and an electrically controlled switch 18 in the proximal end of the haft. The switch 18 can for example be arranged as any of the switches in U.S. Pat. No. 5,423,873 or U.S. 2008/0294218. By arranging a switch of this kind it is possible to have one conductor, the inner wire coil 8 between the proximal end of the lead and the switch, and by control signals control the switch to connect either to the pin 13 or to the helix 4. By switching to the pin during implantation it is possible to measure if the lead is correctly mounted, in which case there will be an electric contact between the pin and the tissue. When it is confirmed that the implantation is properly performed, the switch is connected to the helix to activate the helix as an electrode inside the tissue.

Figure 10:
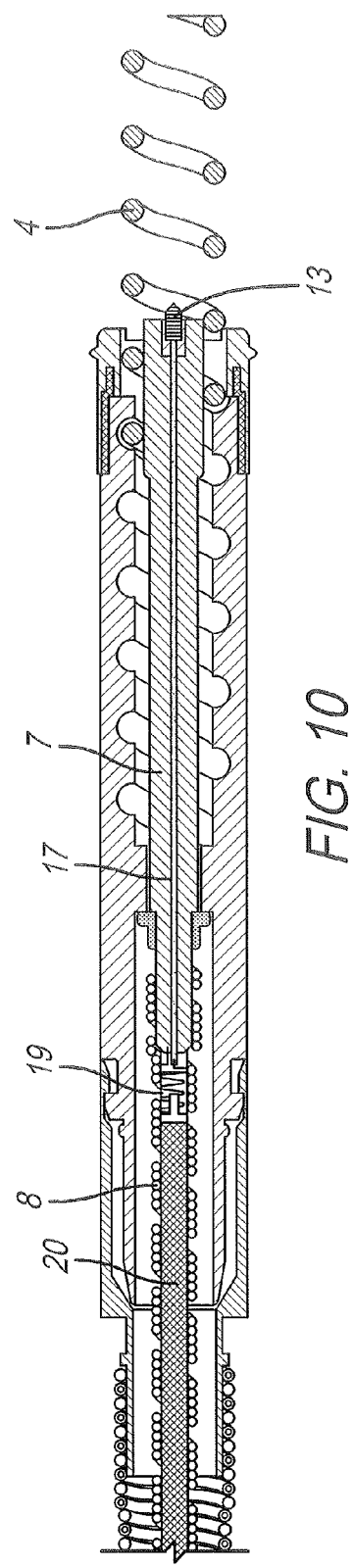
FIG. 10 is a longitudinal section through a distal end of a lead according to a fifth embodiment.
Figure 11:
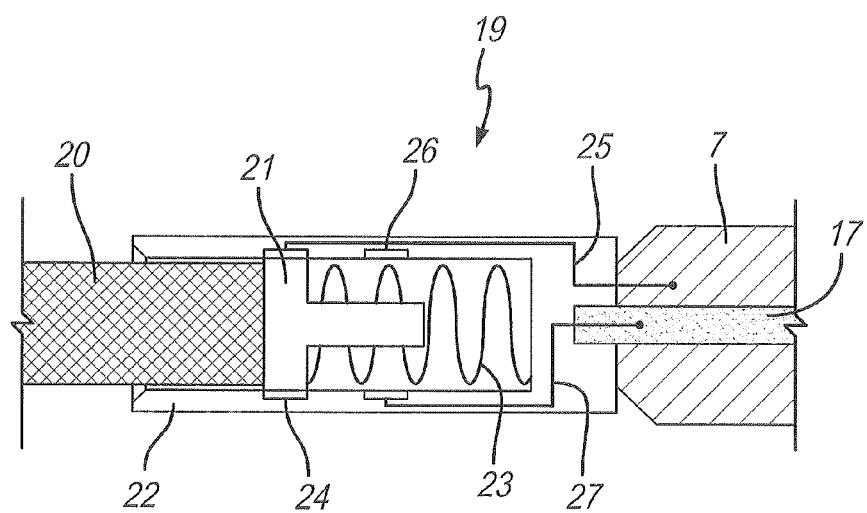
FIG. 11 is an enlarged longitudinal section of a mechanical switch in the embodiment according to FIG. 10.

A fifth embodiment illustrated in FIGS. 10 and 11 is similar to the embodiment in FIG. 9 in that it comprises a switch 19 connecting a conductor 8 between the proximal end of the lead and the switch alternately to the pin 13 or the helix 4. However, in this case the switch is mechanically operated by means of a stylet 20, which can be inserted into an open bore from the proximal end of the lead to the switch. As can be seen from the enlarged longitudinal section of the switch in FIG. 11, it comprises an electrically conducting displaceable member 21, which is accommodated in a sliding manner inside an electrically insulating tubular member 22 and which assumes an initial position according to FIG. 11 by action of a spring 23. The displaceable member 21 is connected to a conductor in the inner coil 8 in a not in the drawings shown way. In the initial position according to FIG. 11, the displaceable member 21 is in electric contact with a first contact member 24 on the inside the tubular member. The first contact member is connected to the helix via the shaft 7 and a wire 25. Also a second contact member 26 is arranged on the inside of the tubular member which is connected to the pin via the insulated conductor 17 inside the shaft 7 and a wire 27. At the time for implantation of the lead it is possible for the physician to 7 operate the displaceable member 21 by pushing the displaceable member to a second position (not illustrated) by means of a stylet 20 where it comes into contact with the second contact member 26. With the displaceable member in the second position it is possible to measure whether the pin 13 is in contact with the tissue or not and as soon as the pressure on the displaceable member from the stylet 20 is released, the displaceable member will return to the initial position and the helix 4 will be connected to the first connector 6 in the proximal end via the conductor in the inner wire coil 8 and will accordingly function as an electrode.

Figure 12:
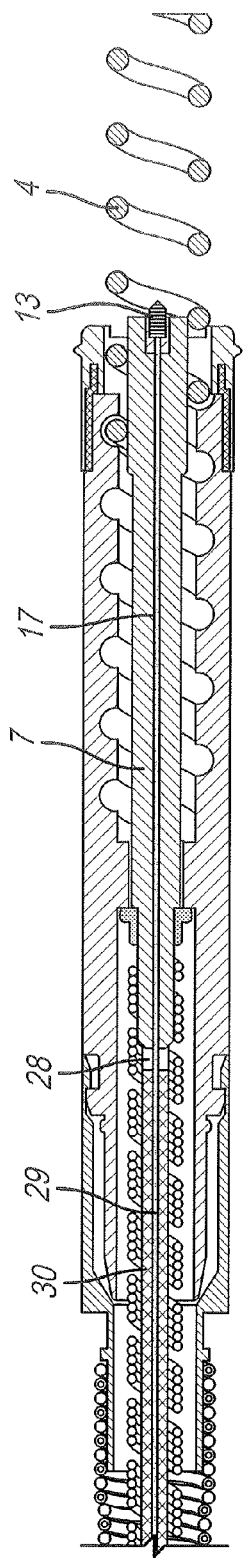
FIG. 12 is a longitudinal section through a distal end of a lead according to a sixth embodiment.

FIG. 12 illustrates a sixth embodiment of the invention. This embodiment is similar to the fourth and fifth embodiments according to FIG. 9 and FIGS. 10-11, respectively. However, it is not provided with any switch in the proximal end of the shaft. Instead, the insulated conductor 17 within the center of the shaft 7, leading from the pin 13, is connected to a contacting member in the proximal end of the shaft. By means of an electrically conducting stylet 29, preferably having a surrounding electrical insulation 30, an electric measuring device at the proximal end of the lead can be brought into electric contact with the pin such that a physician may detect whether the pin is in electric contact with the tissue or not and accordingly whether the helix is screwed sufficient far into the tissue.

Figure 13:
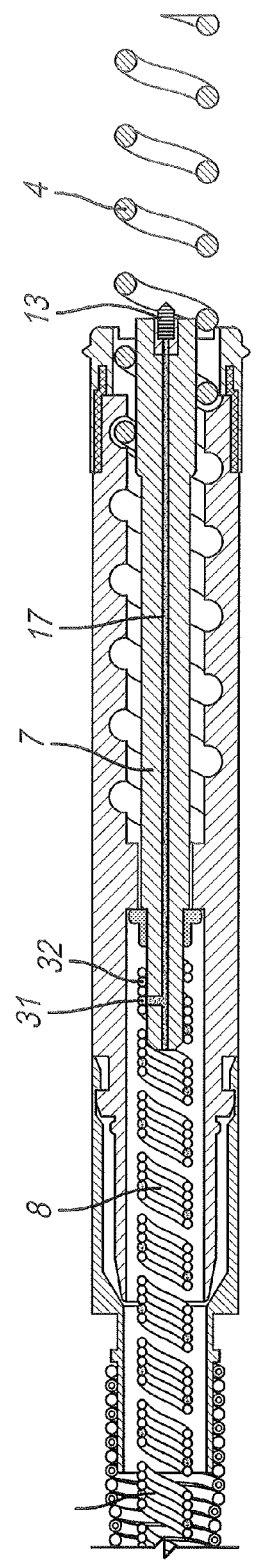
FIG. 13 is a longitudinal section through a distal end of a lead according to a seventh embodiment.

Also in a seventh embodiment according to FIG. 13, the pin 13 is connected to an insulated conductor 17 in the center of the shaft 7. However, in this embodiment, the insulated conductor is connected to a separate insulated wire 31 in the inner wire coil 8, whereas the helix 4 is connected to another separate insulated wire 32 in the same inner wire coil 8. The wire to the pin and the wire to the helix are moreover connected to separate connectors at the connecting structure in the proximal end of the lead (not shown in the drawings). In this way it is possible to connect the pin to a measuring device to detect whether the pin is in electric contact with the tissue or not. When it is assured that the helix is correctly mounted to the tissue, the helix can be connected to the pacemaker or cardiac defibrillating device by connecting it to the corresponding connector.

Figure 14:
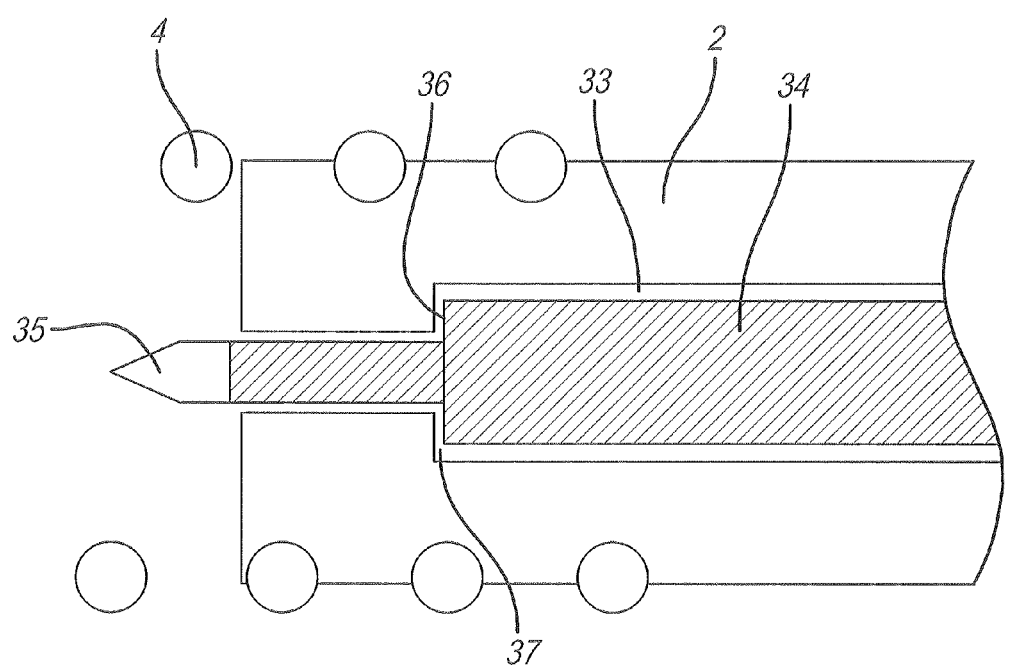
FIG. 14 is a longitudinal section through a distal end of a shaft according to an eighth embodiment.

An eighth embodiment of the invention is illustrated in a schematic longitudinal section of the distal end of the shaft 7 and the proximal end of the helix 4 in FIG. 14. In this embodiment the lead is provided with, in addition to an internal through bore from the proximal end to the proximal end of the shaft, also an internal through bore 33 through the shaft. An electrically conducting stylet 34 is inserted into the through bore from the proximal end of the lead such that a tip 35 of the stylet projects from the distal end of the shaft. According to this embodiment, the stylet 34 can be inserted into the through bore when the distal end of the lead is attached to the heart tissue by means of a helix 4 at a desired position. The tip 35 of the stylet will then function as the second contact surface, the body of the stylet as an electric conductor and the proximal end of the stylet as a connector. Accordingly, by connecting an electric measuring device to the proximal end of the stylet, it can be established whether the tip is in contact with the tissue or not. If it is established that the tip is in contact with the tissue, this is an indication that the helix 4 is properly attached to the tissue. Otherwise the helix is not properly attached. In order to restrict the projection of the stylet from the distal end of the shaft, and accordingly prevent too deep penetration of the stylet into the tissue, it is provided with a stop member in form of a shoulder portion 36, which goes into engagement with a stop member in form of a shoulder portion 37 on the inside of the through bore 33 of the shaft 7. To prevent electric contact of the stylet with the shaft and with the wire coil (8) inside the lead, the stylet is coated with an electrically insulating layer over its entire length except for the tip 35 and the connector surface in its proximal end.

What is claimed is:

1. A medical implantable lead adapted to be implanted into a human or animal body to monitor and/or control an organ inside the body, the lead comprising:
    an intermediate flexible lead part having a lumen, the lumen configured to receive a stylet;
    a connector at a proximal portion of the intermediate flexible lead part;
    a tubular header at a distal portion of the intermediate flexible lead part;
    a rotatable shaft disposed within the tubular header, wherein the rotatable shaft is extendably and retractably arranged relative to the tubular header, and wherein the rotatable shaft has a passageway longitudinally extending from a proximal end to a distal end of the rotatable shaft;
    a first electric conductor electrically coupled to the connector;
    a helix at the distal end of the rotatable shaft, wherein the helix is electrically coupled to the rotatable shaft, and wherein the helix is configured for fixation to the organ upon rotation and extension of the rotatable shaft;
    a pin disposed partially within the central passageway at the distal end of the rotatable shaft, the pin being electrically insulated from the rotatable shaft;
    a second electric conductor disposed within the passageway of the rotatable shaft, the second electric conductor being electrically insulated from the rotatable shaft, and the second electric conductor coupled to the pin; and
    a mechanical switch at the proximal end of the rotatable shaft, the mechanical switch having a first position to electrically connect the first electric conductor to the second electric conductor for electrically activating the pin and having a second position to electrically connect the first electric conductor to the rotatable shaft for electrically activating the helix;
    wherein proper fixation of the helix to the organ is determined by inserting the stylet into the mechanical switch to render the pin electrically active and the helix electrically inactive; and
    wherein upon determination of proper fixation of the helix to the organ, the stylet is removed from the mechanical switch to render the helix electrically active and the pin electrically inactive.

2. The medical implantable lead of claim 1, wherein the mechanical switch comprises:
    an open bore at a proximal end of the mechanical switch to receive the stylet;
    a displaceable member to render the mechanical switch in the first position or the second position.

3. The medical implantable lead of claim 2, wherein the mechanical switch further comprises:
    a first contact member electrically coupling the displaceable member to the helix via the rotatable shaft;
    a second contact member electrically coupling the displaceable member to the pin via the second electric conductor.

4. The medical implantable lead of claim 3, wherein the second contact member is a contact pin extending distally outwardly from a distal end of the displaceable member.

5. The medical implantable lead of claim 1, wherein the pin is coaxially arranged in relation to the helix and projects distally from a distal end of the rotatable shaft.

6. The medical implantable lead of claim 1, wherein the pin is separate from the helix.

7. The medical implantable lead of claim 1, wherein the pin is adapted to penetrate into tissue of the organ.

8. The medical implantable lead of claim 1, wherein a longitudinal length of the pin is less or equal to half a longitudinal length of the helix.

9. The medical implantable lead of claim 1, wherein the pin is disposed centrally on the distal end of the rotatable shaft.

* * * * *